United States Patent
Amsuess et al.

(10) Patent No.: US 11,839,557 B2
(45) Date of Patent: Dec. 12, 2023

(54) PROSTHESIS SYSTEM AND METHOD FOR CHECKING THE FUNCTIONALITY OF A PROSTHESIS SYSTEM

(71) Applicant: Otto Bock Healthcare Products GmbH, Vienna (AT)

(72) Inventors: Sebastian Amsuess, Vienna (AT); Benjamin Gmeiner, Vienna (AT); Matthias Schobesberger, Bas Voeslau (AT)

(73) Assignee: OTTO BOCK HEALTHCARE PRODUCTS GMBH, Vienna (DE)

( * ) Notice: Subject to any disclaimer, the term of this patent is extended or adjusted under 35 U.S.C. 154(b) by 216 days.

(21) Appl. No.: 16/633,109

(22) PCT Filed: Jul. 10, 2018

(86) PCT No.: PCT/EP2018/068624
§ 371 (c)(1),
(2) Date: Jan. 22, 2020

(87) PCT Pub. No.: WO2019/137933
PCT Pub. Date: Feb. 28, 2019

(65) Prior Publication Data
US 2021/0154029 A1 May 27, 2021

(30) Foreign Application Priority Data
Aug. 25, 2017 (DE) .................... 10 2017 119 490.8

(51) Int. Cl.
*A61F 2/72* (2006.01)
*A61F 2/58* (2006.01)
(Continued)

(52) U.S. Cl.
CPC .............. *A61F 2/72* (2013.01); *A61B 5/6811* (2013.01); *A61F 2/583* (2013.01); *A61F 2/76* (2013.01);
(Continued)

(58) Field of Classification Search
CPC .................... A61F 2002/689; A61F 2002/769
(Continued)

(56) References Cited

U.S. PATENT DOCUMENTS

| 5,413,611 A | 5/1995 | Haslam et al. |
| 5,888,213 A | 3/1999 | Sears et al. |

(Continued)

FOREIGN PATENT DOCUMENTS

| CN | 203220464 U | 10/2013 |
| DE | 202010005472 U1 | 9/2010 |

(Continued)

OTHER PUBLICATIONS

"International Search Report and Written Opinion of the International Searching Authority," issued in connection with Int'l Appl. No. PCT/EP2018/068624, dated Sep. 27, 2018 (15 pages).

(Continued)

*Primary Examiner* — David H Willse
(74) *Attorney, Agent, or Firm* — HOLLAND & HART LLP

(57) ABSTRACT

A prosthesis system having at least two sensors, at least one control device, which is coupled to the sensors and processes sensor signals of the sensors, at least one actuator, which is coupled to the control device and can be activated or deactivated on the basis of control signals of the control device, and at least one movably mounted prosthesis component, which can be displaced by the actuator. A standard program, which assigns an actuator action to each sensor independently of the duration and/or intensity of the sensor signal, is stored in the control device or can be called up by the control device.

23 Claims, 2 Drawing Sheets

(51) Int. Cl.
  *A61F 2/76* (2006.01)
  *A61B 5/00* (2006.01)
  *A61F 2/70* (2006.01)

(52) U.S. Cl.
  CPC ... *A61F 2002/701* (2013.01); *A61F 2002/704* (2013.01); *A61F 2002/7615* (2013.01); *A61F 2002/7695* (2013.01)

(58) Field of Classification Search
  USPC .......................................................... 623/912
  See application file for complete search history.

(56) References Cited

U.S. PATENT DOCUMENTS

| | | |
|---|---|---|
| 2002/0143405 A1 | 10/2002 | Davalli et al. |
| 2002/0161451 A1 | 10/2002 | Biedermann et al. |
| 2011/0257765 A1 | 10/2011 | Evans et al. |
| 2011/0264238 A1 | 10/2011 | Van Der Merwe et al. |
| 2014/0288666 A1 | 9/2014 | Gill |
| 2018/0147074 A1 | 5/2018 | Battlogg |

FOREIGN PATENT DOCUMENTS

| | | | |
|---|---|---|---|
| DE | 102015107783 | 11/2016 | |
| KR | 10-2016-0006279 A | * 1/2016 | ............... A61F 2/54 |
| WO | 2007110585 A2 | 10/2007 | |
| WO | 2013088142 A1 | 6/2013 | |

OTHER PUBLICATIONS

Chinese Patent Office, "Office Action", issued in connection with Chinese Patent Application No. 201880053996.9 dated Mar. 30, 2022 (11 pages).

* cited by examiner

PROSTHESIS SYSTEM AND METHOD FOR CHECKING THE FUNCTIONALITY OF A PROSTHESIS SYSTEM

CROSS REFERENCE TO RELATED APPLICATIONS

This application is a U.S. National Entry and claims priority to PCT International Patent Application No. PCT/EP2018/068624, filed 10 Jul. 2018, and entitled PROSTHESIS SYSTEM AND METHOD FOR CHECKING THE FUNCTIONALITY OF A PROSTHESIS SYSTEM, which claims priority to Germany Patent Application No. 10 2017 119 490.8 filed 25 Aug. 2017, the entire disclosures of which are incorporated herein by this reference.

TECHNICAL FIELD

The invention relates to a prosthesis system having at least two sensors, at least one control device, which is coupled to the sensors and processes sensor signals of the sensors, at least one actuator, which is coupled to the control device and can be activated or deactivated on the basis of control signals of the control device, and at least one movably mounted prosthesis component, which can be displaced by means of the actuator. The invention likewise relates to a method for checking the functionality of such a prosthesis system.

BACKGROUND

A prosthesis, and therefore also a prosthesis system according to the invention, is used as a replacement for a missing limb. Besides the replication of an external appearance, prostheses or prosthesis systems are used to provide functions in order as far as possible to fully or at least partially replace the function of the missing natural limb. In prostheses or prosthesis systems, there are devices for fastening the prosthesis device on a stump, for example on a thigh stump or a forearm stump, which are arranged on further prosthesis components. The device for fastening on a stump is configured as a prosthesis socket that comprises a geometrically stable wall, which for example forms a funnel-shaped or buckle-like configuration, in order to receive a stump therein.

Between the stump and the prosthesis socket, a liner may be arranged in order to provide cushioning between the socket wall and the stump. Besides protecting the stump, the liner furthermore serves to ensure a vacuum in the case of a vacuum-based prosthesis socket system, or in order to receive the mechanical locking device inside the stump by a pin-lock system or a strap system. The liner fully encloses the stump. Besides a configuration as a tubular and funnel-shaped liner with a closed distal end cap, a distally open liner may be formed which achieves sealing and alignment at the proximal end of the prosthesis socket and ensures direct contact between a socket inner wall and a stump surface. The liner may be provided with feed-through electrodes or an electrically conductive material configuration, in order to conduct myoelectrical signals from the skin surface through the liner to a prosthesis socket or sensors arranged thereon.

Further prosthetic components are arranged on a prosthesis socket, for example articulations, damping devices, drives and intermediate pieces, for example prosthetic knee joints or lower-leg tubes as well as a prosthetic foot with a prosthetic ankle joint. Prostheses on upper extremities are constructed correspondingly, and are fastened by means of a prosthesis socket on a forearm stump or upper-arm stump. At the distal end of a forearm socket or of a forearm tube, a gripping element or a prosthetic hand may be arranged, which is driven by means of at least one actuator. The actuator is activated or deactivated by a control device, the control device being coupled to sensors which, for example, operate on the basis of myoelectrical signals and allow individually adapted actions to be carried out on the basis of the sensor signals.

In order to be able to use such active prostheses, i.e. ones provided with motor drives, sensors, for example in the form of electrodes, are arranged on the skin surface of the stump or implanted in the limb. In the scope of an elaborate training program, individual myoelectrical signals are then assigned to the respective movements to be carried out, which are brought about by the actuators.

After assembly of the prosthesis system, which is composed of individual components such as sensors, a control device, optionally an amplifier and an actuator, an inner socket, an outer socket, and energy store and an end effector, the finally assembled prosthesis system adapted individually to the respective user must be tested for functionality. To this end, a calibration process is necessary, during which the sensors or electrodes are positioned and the control device is set up so that the received sensor signals lead to a corresponding action. This means that the user must be present for the testing of the functionality of the prosthesis. Because of the fact that a prosthesis user must also first become accustomed to a new prosthesis or a new prosthesis system, it is difficult to check the full functionality of a finally assembled prosthesis system.

SUMMARY

It is an object of the present invention to provide a prosthesis system and a method with which the functionality of a prosthesis system can be checked simply and reliably.

According to the invention, this object is achieved by a prosthesis system having the features disclosed herein and a related method having the features disclosed herein. Advantageous configurations and other embodiments of the invention are disclosed in the description and the figures.

In the prosthesis system according to the invention having at least two sensors, having at least one control device, which is coupled to the sensors and processes sensor signals of the sensors, having at least one sensor, which is coupled to the control device and can be activated or deactivated on the basis of control signals of the control device, and having at least one movable prosthesis component, which can be displaced by means of the actuator, a standard program, which assigns an actuator action to each sensor independently of the duration and/or intensity of the sensor signal, is stored in the control device or can be called up thereby. Driven prosthesis systems consist of a plurality of components, inter alia sensors, a control device and actuators for moving a movably mounted prosthesis component, and optionally an energy store in order to supply the actuators position-independently with energy so that the prosthesis components can be displaced by means of the actuators, generally electric motors. Displacement may in particular be carried out by tilting about a tilt axis, the prosthesis component being tiltably mounted on a base body. As an alternative to tilting, a translation may also be carried out by the actuator. A combination of translation and tilting is likewise possible. Such driven prosthesis systems are based on the evaluation of sensor signals. Sensors may be configured as implanted electrodes or surface electrodes, via which the excitation potentials or activation pulses are received. Such e.g. myoelectrical signals are recorded by the sensors and compared with a stored signal pattern. If there is a match or a sufficiently accurate match between the recorded signal or signal pattern and a stored signal or signal pattern, a corresponding action is executed. In the case of a prosthesis system of an upper extremity, for example a prosthetic hand having a prosthesis socket for fastening on a forearm stump, the actuation may consist in opening or closing a prosthetic hand or a gripping device, for example a so-called hook. The adaptation of such a prosthesis system to the respective user is elaborate and, besides mechanical adaptation via a best possible match of the shape of the prosthesis socket to the arm stump, also comprises a control-technology adaptation during which the signal patterns received by the sensors are assigned to specific actions of an actuator. By tensing and relaxing various muscles or muscle groups, a sequence of movements of the driven prosthesis component may be achieved. To this end, the user of the prosthesis system is instructed to carry out a muscle contraction which corresponds to a particular movement that would be carried out with a natural limb. As soon as a corresponding contraction pattern can be produced with a sufficient selectivity, this pattern is assigned to a corresponding action of the prosthesis component.

If a standard program is stored in the control device of the prosthesis system, or if the standard program can be called up by the control device, it is possible to test the functionality of the entire prosthesis system immediately after assembly. "Calling up" is intended to mean both the initiation of data transmission or the retrieval of data from an external data memory and also the sending of data without a request by the control device. In the event of faults which occur after the adaptation of the prosthesis system to the respective user, it is likewise possible to check where the fault is to be looked for or found. To this end, it is stored in the standard program that an actuator action is assigned to each sensor independently of the duration and/or intensity of sensor signal. After the prosthesis system has been assembled by an orthopedic technician or functional problems of a prosthesis already being used by a patient occur, with the prosthesis system according to the invention it is possible to test rapidly whether all components of the prosthesis system are fully functional or at which position there is a fault. This standard program is also referred to as a standard classifier, which reacts to signals of individual sensors or electrodes with predefined actions or movements of the respective prosthesis component. In order to check the functionality of a prosthesis system, an orthopedic technician must turn on the prosthesis system or the prosthesis and then activate the respective sensor, for example touch it with a finger, a standard operation or a standard action being executed by at least one actuator independently of the duration of the sensor signal or the intensity of the sensor signal, and the prosthesis component being correspondingly displaced. If the intended actuator action is executed, it may be deduced that the energy supply is functioning, the actuator is functioning, all connections are in place and the relevant sensor or the relevant electrode is functional. If the intended actuator action is not executed, there is a defect in this respect which may be further located. Owing to the fact that there are a plurality of sensors in a prosthesis system, particularly electrodes, in turn particularly surface electrodes, which are arranged inside a prosthesis socket or a prosthesis socket system, various actuator actions may be checked. In the case of a prosthesis system of an upper extremity, actuator actions are for example "open the hand", "close the hand", "rotate the hand in one direction" or "rotate the hand in the other direction". The actuation of a respective sensor or of a respective electrode may be simulated in a very simple and controlled way by stroking with a finger.

According to another embodiment of the invention, the number of sensors corresponds to the number of prosthesis components to be displaced, so that each prosthesis component may be checked by activating or deactivating the respective sensors. Each function, which relates to the displacement of a prosthesis component, of the prosthesis system may thus be checked. For the tilting of a prosthesis component about a uniaxial articulation, only two sensors are required, which carry out a displacement in one direction and the opposite direction. For more complex systems, for example a prosthetic hand, a greater number of sensors is required. If there are more sensors or electrodes than movable prosthesis components, for example in order to achieve more accurate discrimination of the signal patterns because of a greater number of sensors, some sensor signals may be assigned doubly to a prosthesis component, or a combination of a plurality of movements takes place, for example "rotate the hand" and "open the hand", so that a combination of sensor signals and commands is tested.

It is furthermore possible that the standard program operates all functions of the prosthesis component, in order to ensure that the prosthesis system can be checked fully in respect of its functionality. Thus, after the prosthesis system is assembled and activated by turning on all the sensors in succession, for example by touch-sensitive electrodes being stroked in succession, the prosthesis system executes all movements in succession so that the person carrying out the test knows that all the electrodes or sensors are connected in the right sequence.

Furthermore, the person carrying out the test finds out that all the sensors or electrodes have a good contact, that the control device is functioning correctly and that in principle pattern recognition takes place. It is furthermore demonstrated that an energy store or a plurality of energy stores is or are connected correctly, that the prosthesis components are assembled correctly and that articulations are movable or translatable and are controlled. Furthermore, it may be ascertained that there are no incorrect cable connections, no plug cable defects, no defects or contact defects, so that a complete check may be carried out within a short time for the entire prosthesis system from the sensor input to the movement output, without complicated evaluation software having to be connected or stored. If the test is passed, the prosthesis system is technically in a faultless state so that a functionality check may be carried out without prior individualization to the user.

The sensors are preferably configured to be touch-sensitive so that in this way a simple and rapid check of the prosthesis system may be carried out. The control device is freely programmable, so that after the check and independently of the possibility of a check with a standard program, pattern recognition software for the detection of signal patterns on the basis of the sensor data may be programmed and adapted individually for each user of the prosthesis system.

Each sensor may be assigned precisely one actuator action, so that it is possible to establish clearly whether all the sensors are functional. The actuator action may also be a combined action consisting of a plurality of movements of a plurality of prosthesis components. For the possibility of easier discrimination and checking whether the prosthesis system is functional, each sensor is assigned an individual actuator action in order to prevent a malfunction of a sensor or of an electrode from remaining unnoticed.

The sensor device may comprise an interface, in particular a wireless interface, to an operating device such as a cellphone, a tablet computer, a computer, so-called wearable devices such as smart watches for smart glasses, or similar device. As an alternative or in addition, the control device may comprise an interface, in particular a wireless interface, to a display device in order to extend the checking function. The interface allows data be transported to the prosthesis system and from the prosthesis system to an operating device and/or a display device, so that improved checking of the functionality may be carried out. If, for example, no connection is set up between the operating device or the display device and the control device even though the prosthesis system is turned on, the control device is defective or the control device is not connected correctly to the energy store. If it has been possible to set up a connection and the prosthesis system is in a checking mode in which the standard program has been activated, a reactivity of the sensor device or electrodes may be checked and displayed. By means of the operating device, which may be coupled to the prosthesis via a radio link, control signals may furthermore be generated as a specification for the actuators and sent to the control device. If no reporting takes place, for example after turning on the prosthesis or touching the sensors or the sensor, a lack of electrical connection is displayed on the operating device, for example a tablet or a cellphone. It may be deduced from this that either the sensor is defective or a plug connection or the like has been disconnected. A corresponding error message is then output on the operating device or a separate display device. Similarly, further checks may be carried out and represented straightforwardly, for example the activity of the sensors or electrodes when stroking with a finger. If an actuator action or movement of the prosthesis does not take place despite stroking and establishment of sensor or electrode activity, the error must be located downstream of the sensors, for example a disconnected plug contact, or the motor or the prosthesis mechanism is defective. By means of the operating device, a movement command may be delivered directly to the control device. If the prosthesis does not react, the error lies with the prosthesis or the wiring, while if the prosthesis component moves the error lies with the electrodes or sensors.

According to one embodiment of the prosthesis system, a software application, which is configured to run on a processor of the operating device, is installed in the operating device, the software application being configured to display functions of the prosthesis system, to visually check and/or display sensor signals, to trigger actuator actions by signals sent to the control device, to output error, warning and/or advice messages, and/or to output procedural instructions for carrying out a check of the functionality of the prosthesis system. The software application makes it possible, for example, to display system functions, for example by means of optical and acoustic display devices. Often, such a software application may be installed on a tablet or a smartphone and may run there on a corresponding processor. In the case of visual display of system functions, a visual check of the sensor signals may be carried out, for example by representation of the signal path or by an optical representation that control signals or simulated sensor signals, which have been transmitted from the operating device to the control device, are tracked. Particularly in the case of a configuration of the operating device with a touchscreen, it is possible to trigger actuator actions or movements of the actuators by signals sent to the control device, i.e. control signals or simulated sensor signals which are recognized as control signals. The triggering may be carried out manually, for example on a user interface on which the prosthesis system and/or the individual sensors or electrodes are represented. By means of the software application, reporting in respect of possibly existing errors, risks or general information may also be carried out in the operating device. In this way, it is possible to provide the patient or the orthopedic technician with reports of whether errors exist, whether errors or risks are to be expected, and whether further aspects are to be taken to account in the safety check or during use and maintenance of the prosthesis system.

The software application may output instructions for carrying out the individual steps for checking the functionality of the prosthesis system, in a similar way to operating instructions with a decision tree, by means of which various further steps may be proposed as a function of the respective reports of the components of the prosthesis system, and have to be carried out.

In one embodiment of the invention, the control device is configured in such a way that, after activation of the standard program and triggering of a sensor signal, an actuator action is induced and the execution or non-execution thereof is recorded and/or the presence or absence of a sensor signal is output on an output device. The control device is connected to the actuators or sensors or feedback devices, by means of which it is recorded and sent to the control device whether an action has been executed. A check is furthermore made, and recorded via feedback, whether a control signal or sensor signal is present and has been output. For the checking, for example by a technician, an output device is driven and the report is output.

In the method for checking the functionality of a prosthesis system having a plurality of sensors, at least one control device, which is coupled to the sensors and processes sensor signals of the sensors, at least one actuator, which is coupled to the control device and can be activated or deactivated on the basis of control signals of the control device, at least one movably mounted prosthesis component being displaceable by means of the actuator, a standard program, by which an actuator action is assigned to each sensor, preferably independently of the duration and/or intensity of the sensor signal, after activation of the standard program and triggering of a sensor signal, an actuator action being induced and the execution or non-execution thereof being recorded and/or the presence or absence of a sensor signal being output on an output device, is stored in the control device or can be called up thereby. If, after the triggering of a control signal, the actuator action is assigned to the respective control signal is executed, successful assembly may be deduced. If the actuator action is not executed, a defect of the prosthesis system, which may be located because of the specific assignment of a sensor signal to an actuator action, may be deduced therefrom. The activation may be carried out by means of touching the sensor or the sensors or by means of an operating device coupled to the prosthesis, the output or display relating to the presence or absence of a sensor signal or of a feedback from the prosthesis to the operating device being carried out on the output device. The output device is preferably coupled to the operating device, in particular a display on a tablet or a cellphone. As an alternative or in addition, the output device may send information of whether a sensor signal has been triggered, whether an activity of the sensors can be established and/or an action has been executed, acoustically or in another way. To this end, one sensor per remote command may be stimulated with an electrical pulse by the operating device. The reaction of the sensor, i.e. the generation and forwarding of a sensor signal to the control device, may be recorded and evaluated.

According to another embodiment, when a control signal is triggered, a prosthesis component is displaced maximally in a displacement direction. If a displacement of the prosthesis component assigned to the control signal is actually carried out after the triggering of the control signal, the entire mechanical movement range may be checked because of the fact that a full movement is executed, i.e. for example a maximum rotation in one direction or the other direction. If the corresponding movement is not executed, or is executed only partially, the mechanical components of the prosthesis system would need to be checked.

According to another embodiment of the method, before the execution of an actuator action, a check is made as to whether the number of sensors stored in the standard program are actually coupled to the control device. This checking may be carried out immediately after the prosthesis system is turned on. After the prosthesis system is turned on, the prosthesis system may be coupled to an external display device and/or operating device, in particular via a wired or wireless interface. As soon as it has been possible to set up a connection and the prosthesis system is in the checking mode, a display of the sensor activity or electrode activity may be carried out, in order to check whether all the electrodes or sensors are coupled to the control device, optionally via an amplifier.

The sensor signals may be amplified by an interconnected amplifier or an amplifier circuit, so that they can be evaluated more easily in the control device.

For each executed or not executed actuator action, a report may be sent to an operating device and/or display device, which is coupled to the control device via an interface, in particular a wireless interface.

The standard program may be activated by means of a switch or a signal of an external operating device, before a sensor signal is generated. The prosthesis system is therefore brought into a checking mode, in which the prosthesis system is checked for functionality, before or after individualization is carried out by adaptation of the pattern recognition software.

The sensor signal may be triggered by activation of a sensor, for example by touching, proximity of a body part or other manipulation by a person carrying out the test, for example an orthopedic technician. A check is therefore made as to whether the sensor or the electrode per se is functioning correctly, i.e. the component is in a technically faultless state. To this end, the electrode or the sensor is used and handled as is the case during conventional use. It is likewise possible that a signal for activating a drive is sent directly from an operating device to the control device, so that a complete check of the prosthesis may be carried out even if sensors are not functioning or signals of sensors cannot be forwarded.

Preferably, in the checking mode, the actuator action is assigned to the respective sensor independently of the duration and/or intensity of the sensor signal, so that in the case of already individualized prosthesis control an orthopedic technician does not have to generate exactly the signal pattern of the respective patient in order to be able to carry out a check. In the standard program, it is sufficient to generate any desired signal, so that the checking of the prosthesis is made easier.

Since multichannel controls are being used evermore frequently, by means of which a larger number of control commands can be generated, up to eight surface electrode pairs being used to control a prosthetic hand, for example, according to another embodiment a plurality of sensors are activated simultaneously or successively in a predetermined period of time, and an actuator action is induced or output which differs from the actuator action or actuator actions which is or are induced or output in the event of a single activation. Thus, for example, by stroking two electrode pairs a different function may be triggered than by separate stroking or activation of the sensors or electrode pairs at different times, so that in the case of complex prostheses having a multiplicity of functions each of these functions may be checked even if there are fewer sensors or electrode pairs than functions. Thus, for example with three electrode pairs up to six functions of a prosthesis may be checked by simultaneous actuation or activation of electrode pairs or individual activations of electrodes.

According to another embodiment of the method, a software application which is configured to generate a control signal or to simulate a sensor signal, which is sent to the control device, is run on a processor. In this way, it is possible to manually trigger actuator movements or actuator actions by signals being sent to the control device, for example by touching a button on a touchscreen. Due to the manual generation of a control signal or of a simulated sensor signal, it is possible to check each function and each sensor individually. Each control signal may be generated individually and separately on or in the operating device or at another input position on the prosthesis system, and sent to the control device.

The software application may be configured to display system functions on a display or to output them by means of another output device, for example by means of a tactile output device or an acoustic output device. The software application may also be configured to display control signals or simulated sensor signals on a display, in order to obtain feedback relating to which control signals or simulated sensor signals have been generated, where these have been sent, and which actuator actions have thereupon been executed.

The software application may likewise be configured to output error, warning and/or advice messages via an output device, for example by means of a display or a loudspeaker which is formed in the operating unit or as part of the prosthesis system.

With the prosthesis system according to the invention and with the method according to the invention, simple checking of the sensor, electrical, electronic and mechanical system is possible both before and after use on the patient and individualization. An orthopedic technician may therefore check, before the elaborate adaptation of the control to the patient, whether the prosthesis is in principle functional, whether all the plugs or connections are intact, and whether and where faults occur. These faults may be located, so that repair or correction is simplified. Likewise, the error search in an already individualized prosthesis is made easier. Remote maintenance or remote diagnosis may also be carried out via the operating device, without the orthopedic technician having to be on site, which reduces the time outlay for a repair. It is possible to check whether all the components are present without adaptation to a patient having to have been carried out. In particular, sensors, actuators and cables, connections as well as optionally an energy store and the mechanical components of the prosthesis device are checked. After turning on, the respective components may give a report or actively report that they are connected.

BRIEF DESCRIPTION OF THE DRAWINGS

The invention will be explained in more detail below with the aid of the appended figures, in which.

DETAILED DESCRIPTION

Figure 1:
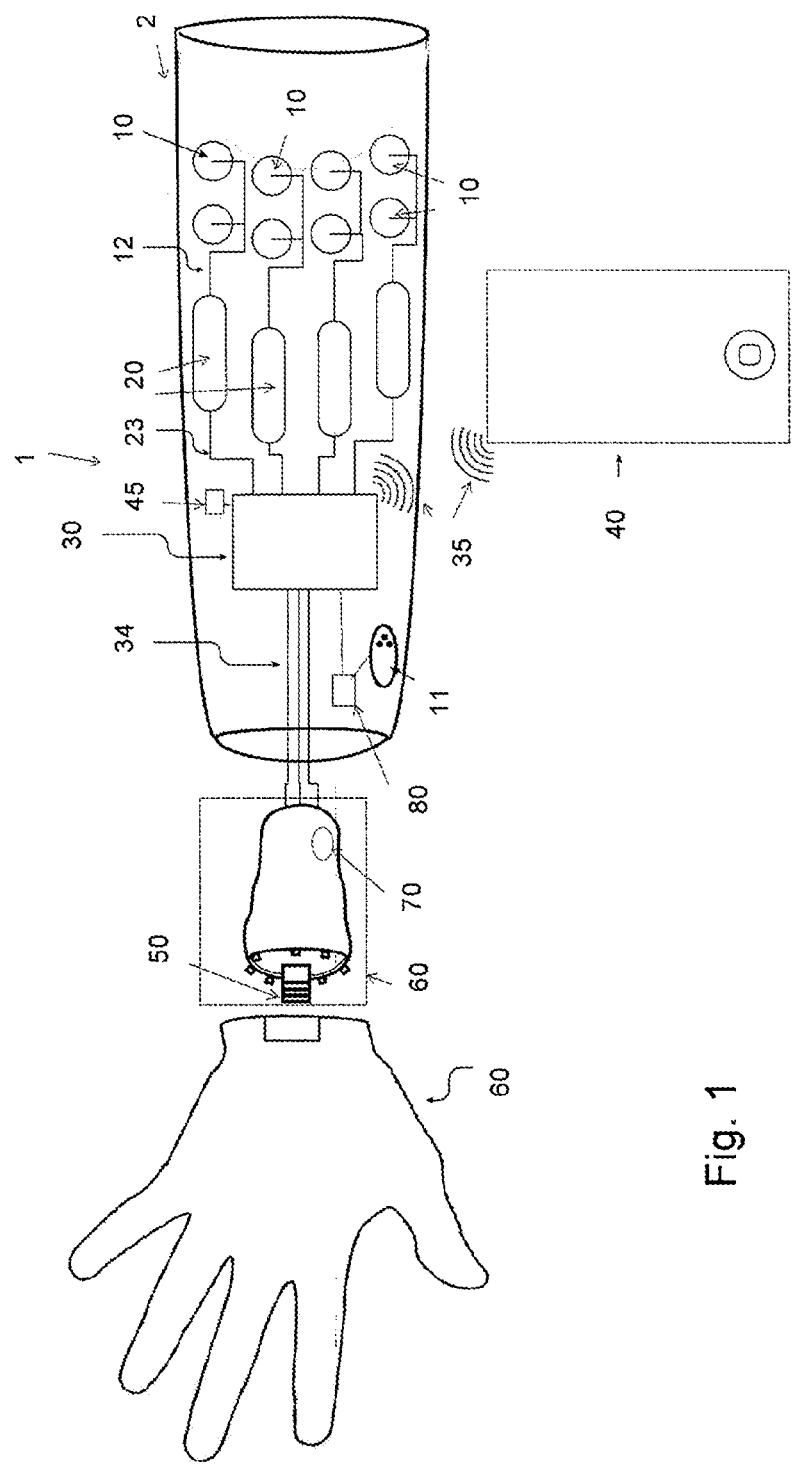
FIG. 1 shows a schematic representation of a prosthesis system.

FIG. 1 shows a schematic representation of an exemplary representation of a prosthesis system 1 in the form of a prosthetic hand system, having a prosthesis socket 2 by means of which the prosthesis system can be fastened on a forearm stump. As an alternative to configuration as the prosthesis of an upper limb, it is possible and provided to configure the prosthesis system 1 as a prosthesis of a lower limb. It is likewise possible to configure the prosthesis socket 2 to receive an upper-arm stump. A multiplicity of sensors 10 in the form of surface electrodes are arranged inside the prosthesis socket 2, four electrode pairs being arranged as sensors 10 on the inner surface of the prosthesis socket 2 in the exemplary embodiment represented. By means of the sensors, myoelectrical signals may be received during muscle contractions. The sensors 10 record surface potentials and may also be touch-sensitive. Furthermore, for each electrode pair, an amplifier 20 is provided in the prosthesis socket 2 or on the prosthesis socket 2, this amplifier being connected to the electrode pair by means of a line 12. From the amplifier 20, a connection to a control device 30 is established by means of a line 23, so that sensor signals are sent from the sensors 10 via the line 12, the amplifier 20 and the line 23 with the control device 30. Likewise connected to the control device 30 is a switch 45 for activating a standard program, which is stored in the control device 30.

In the control device 30, an interface 35 is formed for connecting the control device 30, and therefore the prosthesis system 1, to an external operating device 40, for example in the form of a cellphone, a tablet or a computer. Instead of a wireless interface 35, as shown in the exemplary embodiment represented, this may also be done via a plug connection.

An on/off switch 11 is arranged on the prosthesis socket 2, in order to activate or deactivate the electrical and electronic system of the prosthesis system 1. The switch 11 is coupled to an energy store 80 which is arranged in the prosthesis socket 2 and by means of which, on the one hand, the control device 30 and the amplifier 20 and, on the other hand, an actuator 70 are supplied with electrical energy. The actuator 70 comprises at least one electric motor, which can be activated and deactivated on the basis of control signals which are conveyed via lines 34 from the control device 30 to the actuator 70. In the finally assembled state, the actuator 70 is part of the prosthesis system 1 and is preferably mounted inside the prosthesis socket 2 or inside an actuable prosthesis component 60, which is part of the prosthesis system. In the exemplary embodiment represented, the prosthesis component 60 is configured as a prosthetic hand which can be driven by means of the actuator 70, although it may also be configured as a different prosthesis component, for example as a so-called hook, an individual gripping claw, a different prosthesis of the upper extremity or as a prosthesis of the lower extremity, for example as a prosthetic foot, which is then activated no longer by means of electrodes 10 on the forearm but, for example, on the lower leg. With the prosthetic hand 60, various operations may be carried out, and for example the prosthetic hand 60 may be rotated relative to the prosthesis socket 2 in order to allow displacement about a rotation axis directed parallel to the longitudinal extent of the prosthesis socket 2. Likewise, one or more prosthetic fingers of the prosthetic hand 60 may be moved by the actuator 70, so that a closing movement or an opening movement of the prosthetic hand 60 may be carried out.

After assembly, the actuator 70 is located inside a prosthesis connector 50, which is in turn located inside the prosthesis socket 2. The prosthesis component 60 is fastened on the prosthesis connector 50. In addition, it is possible for further drives or actuators, articulations, force transmission devices, gearing devices and the like to be arranged inside the prosthesis component 60. Furthermore, other energy stores 80 may be fastened on or inside the prosthesis socket 2 and coupled to the electrical and electronic components. The prosthesis socket 2 may be configured in several parts and, for example, comprise an inner socket and an outer socket in order to form the prosthesis socket 2. The outer socket represents a mechanically highly loadable tubular or conically widening socket for a stump of a limb and provides fastening devices for the mechanical components and, in particular, the at least one prosthesis component 60. An inner socket is formed from a comparatively softer resilient material and is used to establish direct contact with the skin surface of the stump. The sensors 10 or electrodes are then fastened on the inner socket, so that during final assembly, in particular when fitting together the outer socket and the inner socket, it may happen that a cable is disconnected or breaks. In conventional prosthesis systems which operate on the basis of pattern recognition, such an error can be found only by putting the prosthesis on the patient, starting a calibration process and testing all of the control signals in cooperation with the user. This means that the user or patient must be present during assembly or functional checking of conventional prosthesis systems. In particular, in the event of an inexperienced user, errors of the conventional prosthesis system cannot be identified clearly since control errors may be caused by unaccustomed contractions.

Since a standard classifier or a standard program, which reacts to activities of individual electrodes or sensors 10 with predetermined movements of the prosthesis component 60, independently of whether other electrodes or sensors 10 are activated and how long or how intensely a sensor signal is output, is stored in the control device 30, it is possible to check the prosthesis system 1 fully for functionality in a straightforward way. The standard program in the control device 30 reacts to an activity of a first electrode 10 and with the action "open the hand", the activity of a second electrode 10 with "close the hand", the activity of a third electrode 10 with "rotate the hand upward" and the activity of a fourth electrode 10 with "rotate the hand downward". The activation of an individual electrode or of a sensor 10 may be simulated by simple and deliberate stroking or touching with a finger, so that an actuator action is executed when a sensor signal is triggered by contact with a finger or the like.

For a simple functional check, after assembly of the prosthetic system 1, an orthopedic technician would turn it on by means of the on/off switch 11 and then successively stroke all the sensors 10 or electrode pairs 10 with a finger. If the prosthesis system fully executes the intended movements successively with the prosthesis component 60 or the prosthetic hand 60, the orthopedic technician knows that all the sensors 10 or electrodes are connected in the correct sequence, that these sensors 10 or electrodes have a good contact, that amplification of the signals takes place in the amplifier 20, and that the control device 30 is connected to the sensors 10 in the form of the electrodes. In the event of full execution of the intended movements, it is thereby also shown that the control device 30 is functioning correctly and pattern recognition is in principle carried out, and that the driving of the prosthesis component 60 can take place in any direction. The energy stores 80 are connected and the mechanical components of the prosthesis component 60, i.e. articulations, force transmission devices, gearings, telescope device or the like are correctly connected and are driven as intended. After turning on by means of the switch 11 and stroking the sensors 10, the entire prosthesis system with mechanisms, electricals and electronics is checked fully in a very short period of time. In order to activate the standard program stored in the control device 30, or the standard classifier, the corresponding program may be activated or deactivated by means of the switch 45. Thus, after switching on by means of the on/off switch 11, the standard program may initially be carried out by means of activating the selector switch 45, before the sensors 10 are touched. After the end of the checking, the standard program is turned off so that calibration of the prosthesis system 1 for the respective prosthesis user may be carried out. To this end, the control device 30 is freely programmable or trainable in the scope of pattern recognition.

If all the movements, provided in the standard program, of the prosthesis components have been executed correctly, an orthopedic technician may be sure that the prosthesis system 1 is in an electrically, electronically and mechanically faultless state, before it is delivered to the end user.

As an alternative or in addition to a mechanical switch 45, the standard calibrator or the standard program may be sent via the interface 35 to the control device before the checking of the prosthesis system 1 is carried out.

If the checking has not been successful, i.e. at least one of the prosthesis components 60 does not execute the intended actions or actuator actions, the orthopedic technician may carry out a corresponding correction or repair. This type of testing is advantageous in particular when reconfiguring a prosthesis. In addition or as an alternative, extended checking may be carried out via remote control and/or in the case of an adapted prosthesis already adjusted for the patient, with the control, in order to identify the error source. The possible procedure for this is represented in the flowchart according to FIG. 2.

First, after turning on by means of the switch 11, in a step A operating device 40 in the form of, for example, a cellphone, tablets, wearable device or computer is coupled to the control device 30 via the interface 35. The interface 35 may be configured as a wireless interface or also as a wired interface. In a query B, a check is made of whether it has been possible to set up a connection between the operating device 40, which also comprises an optical display, and the control device 30. If this is not the case, in step C it may be established that the control device 30 is defective.

If it has been possible to establish a connection, this leads to the checking mode being set up in step D. First, a query is made as to whether all the sensors 10 or all the electrodes are connected to the control device 30. If this is not the case, the connecting line 23 to the amplifier 20 or the amplifier 20 itself is defective, which is output in step F. If all the sensors 10 or electrode pairs have been detected and connected, the standard classifier is activated in the control device 30 or loaded into the latter. This is done in step G. Subsequently, the sensors 10 or electrodes 10, which are configured as skin electrodes, are successively touched with a finger or stimulated electrically or electronically, which is done in step H.

If all the prosthesis components 60 move in the intended way and in the intended sequence, which is queried in step I, and the last electrode has been checked, which is queried in step J, the prosthesis system 1 is assembled correctly and operational, which is output in step K. If the last electrode or sensor 10 has not yet been checked, i.e. not all the electrodes have been touched or stimulated, the procedure is repeated from step H until the last electrode has been interrogated. Steps G to K may preferably also be carried out without the external operating device 40. Each individual electrode or each individual sensor 10 is therefore checked individually by the method. There may be a plurality of prosthesis components 60 in the prosthesis system, for example electrical elbows or electrical knee joints or ankles. Each prosthesis component 60 may contain one or more actuators 70. In the prosthesis system which comprises a prosthetic hand, a component 60 and a prosthesis connector 50 may be formed together with the actuator 70 for moving the prosthetic hand. The actuator 70 is responsible for moving the prosthetic hand in the region of the wrist, in order to carry out a rotation about a rotation axis. There may also be a plurality of actuators 70 in order to be able to execute a plurality of different rotational movements. Different rotational movements may also be executed with only one actuator 70. In addition, the prosthetic hand per se is a prosthesis component 60 in which a plurality of actuators 70 may be arranged in order to move the prosthetic fingers relative to a chassis. Actuators 70 may also be arranged inside the prosthetic fingers in order to move phalanges relative to one another and/or relative to the chassis. A plurality of components 60 may be combined or combinable to form the prosthesis system. Besides at least one actuator, each prosthesis component may also have at least one connector 50, which is used in order to connect the components to one another or to the prosthesis socket 2.

If the prosthesis component 60 does not execute the correct movements in the checking step I, a query is made in step L as to whether the corresponding electrode or the corresponding sensor 10 has been classified as active in the operating device 40 or in the app. If this is not the case, the connection 12 from the electrode 10 to the amplifier 20 is defective, which is displayed in step M.

If the electrode 10 is displayed as active in the operating device 40, in step N the desired movement of the prosthesis component 60 is triggered manually or in the operating device 40. In step O a query is carried out as to whether the prosthesis component 60 executes the desired movement or the desired movements fully and in the correct sequence. If this is not the case, the connection 34 from the control device 30 to the actuator 70 is defective, which is output in step P. If the prosthesis component 60 executes the respective predetermined movement correctly, it may be identified in step Q that the pattern recognition software inside the control device 30 is defective.

If the operating device 40 does not display any possibility of connection to the prosthesis system 1 even though the former has been turned on by means of the switch 11, either the plug from the control device 30 to the actuator 70 is disconnected or the control device 30 is defective.

If patient calibration data have already been stored in the control device 30 or in the prosthesis system 1, the standard program or the standard classifier may be activated by means of the operating device 40 or transmitted into the prosthesis system 1.

If the sensors 10 are stroked with a finger or activated in another way in step H, stroking with the finger or activation is for example represented by an icon on the operating device 40. If an icon indicates no activity when stroking or activating the corresponding electrode, the orthopedic technician may deduce an error of this electrode or of this sensor 10. If all the electrodes are correctly displayed as active during stroking or activation but the corresponding prosthesis movement does not take place, the error lies in a cable connection being defective or the prosthesis component 60 being defective. If a movement command, for example "open the hand", is sent directly by means of the operating device 40 or the checking software and the prosthetic hand 60 does not react, the error lies not in the software or in the electronics but in a defective cable connection, in a defective actuator unit 70 or in the prosthesis component 60. If the prosthesis component 60 moves as a result of the command via the separate operating device 40 but not when stroking or activating the sensors 10 actually intended therefor, the sensors 10 are defective.

Figure 2:
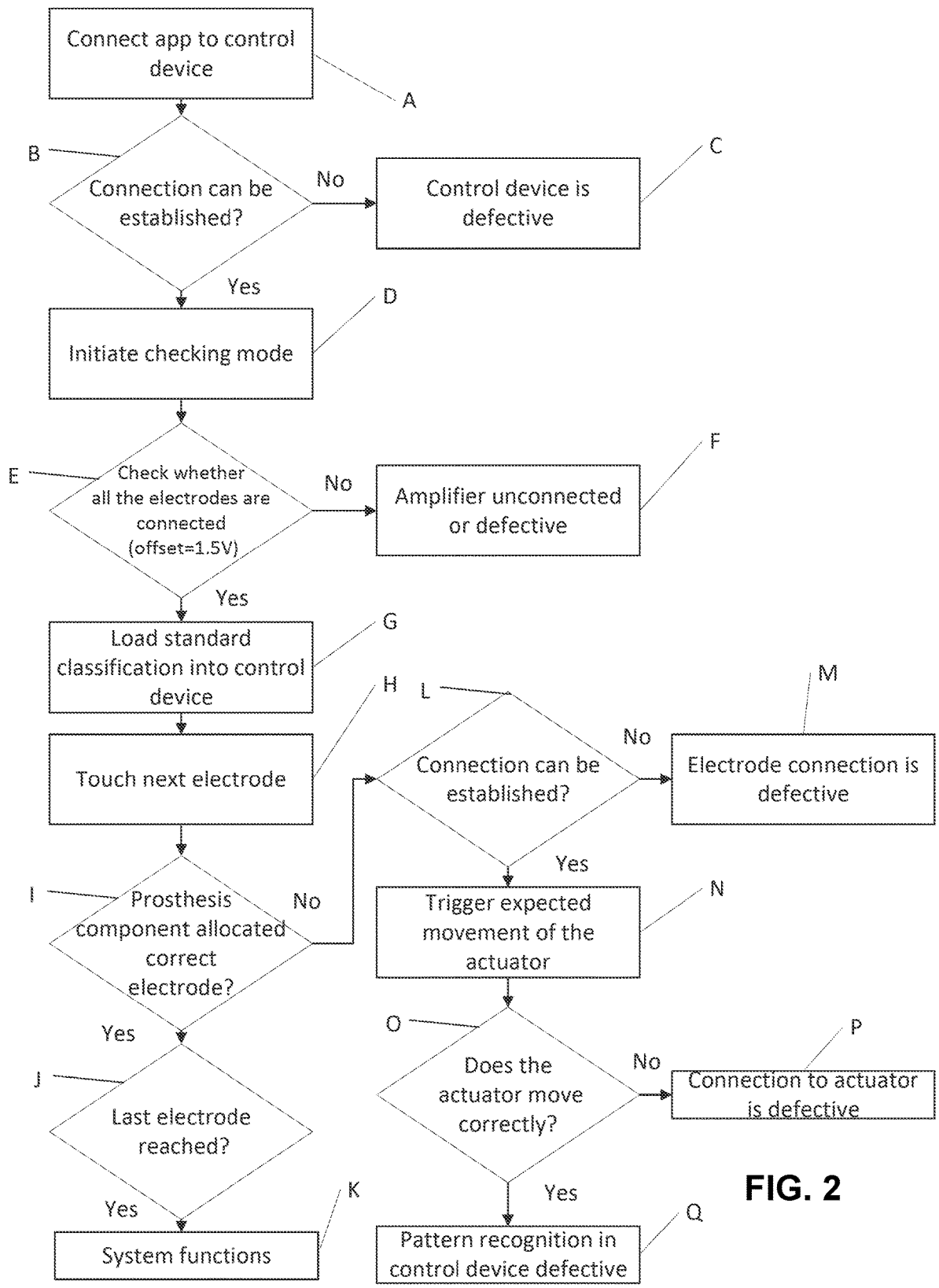
FIG. 2 shows a flowchart of a check.

By running through the checking plan according to FIG. 2, correct functioning and functionality of the prosthesis system may be ensured very rapidly or, if an error occurs, the error source may be identified rapidly and eliminated straightforwardly, so that a rapid error correction may be carried out after disassembling the prosthesis system.

We claim:

1. A prosthesis system comprising:
   at least two sensors;
   at least one control device, which is coupled to the sensors and processes sensor signals of the sensors;
   at least one actuator, which is coupled to the control device and can be activated or deactivated on the basis of control signals of the control device;
   at least one movably mounted prosthesis component, which can be displaced by the actuator; and
   a standard program, which assigns an actuator action to each sensor independently of at least one of the duration and intensity of the sensor signal, is stored in the control device or can be called up by the control device, wherein the control device is freely programmable to execute a pattern recognition, and wherein the standard program is different from an application program.

2. The prosthesis system according to claim 1 wherein the standard program operates all functions of the at least one prosthesis component.

3. The prosthesis system according to claim 1, further comprising an energy store, which is coupled to the at least one actuator and integrated in the prosthesis system or assigned to the prosthesis system.

4. The prosthesis system according to claim 1, wherein the sensors are configured to be touch-sensitive.

5. The prosthesis system according to claim 1, wherein only one actuator action is assigned to each sensor.

6. The prosthesis system according to claim 1, wherein an individual actuator action is assigned to each sensor.

7. The prosthesis system according to claim 1, wherein the control device comprises an interface to at least one of an operating device and a display device.

8. The prosthesis system according to claim 7, wherein a software application, which is configured to run on a processor of the operating device, is installed in the operating device, the software application being configured to display functions of the prosthesis system, to at least one of visually check and display sensor signals, to trigger actuator actions by signals sent to the control device, to output at least one of error, warning and advice messages, and to output procedural instructions for carrying out a check of the functionality of the prosthesis system.

9. The prosthesis system according to claim 1, wherein after activation of the standard program and triggering of at least one sensor signal, the control device induces at least one actuator action and at least one of records the execution or non-execution thereof and outputs the presence or absence of a sensor signal on an output device.

10. A method for checking the functionality of a prosthesis system, the method comprising:
    providing a plurality of sensors, at least one control device, which is coupled to the sensors and processes sensor signals of the sensors, at least one actuator, which is coupled to the control device and can be activated or deactivated on the basis of control signals of the control device, at least one movably mounted prosthesis component being displaceable by the actuator, and a standard program, by which an actuator action is assigned to each sensor; and
    after activation of the standard program and triggering of a sensor signal, an actuator action is induced and at least one of the execution or non-execution thereof is detected and recorded and the presence or absence of a sensor signal is output on an output device, is stored in the control device or can be called up by the control device.

11. The method according to claim 10, wherein, when a sensor signal is triggered, a prosthesis component is displaced maximally in a displacement direction.

12. The method according to claim 10, wherein, before the execution of an actuator action, a check is made as to whether the number of sensors stored in the standard program are coupled to the control device.

13. The method according to claim 10, wherein the sensor signals are amplified.

14. The method according to claim 10, wherein for each executed or not executed actuator action, a report is sent to at least one of an operating device and a display device.

15. The method according to claim 10, wherein the standard program is activated by a switch or a signal of an external operating device, before a sensor signal is received or measured.

16. The method according to claim 10, wherein the sensor signal is sent to the control device by activation of a sensor or by an operating device.

17. The method according to claim 10, wherein the actuator action is assigned to the respective sensor independently of at least one of the duration and intensity of the sensor signal.

18. The method according to claim 10, wherein a plurality of sensors are activated simultaneously or successively in a predetermined period of time, and an actuator action is induced or output which differs from the actuator action which is induced or output in the event of a single activation.

19. The method according to claim 10, wherein a software application which is configured to generate a control signal or to simulate a sensor signal, which is sent to the control device, is run on a processor.

20. The method according to claim 19, wherein the software application is configured to display system functions on a display or to output the system function by another output device.

21. The method according to claim 19, wherein the software application is configured to display control signals or simulated sensor signals on a display.

22. The method according to claim 19, wherein the software application is configured to output at least one of error, warning and advice messages via an output device.

23. The method according to claim 19, wherein the software application is configured to specify various method steps via an output device and to carry out the method steps.

\* \* \* \* \*